(12) United States Patent
Cooper et al.

(10) Patent No.: US 10,954,527 B2
(45) Date of Patent: Mar. 23, 2021

(54) LIMITED TRANSPIRATION TRAITS AND BREEDING METHODS IN MAIZE

(71) Applicants: PIONEER HI-BRED INTERNATIONAL, INC., Johnston, IA (US); NORTH CAROLINA STATE UNIVERSITY, Raleigh, NC (US)

(72) Inventors: Mark Cooper, Johnston, IA (US); Carlos Messina, Des Moines, IA (US); Thomas Sinclair, Raleigh, NC (US); Graeme Hammer, Brisbane (AU)

(73) Assignees: PIONEER HI-BRED INTERNATIONAL, INC.; NORTH CAROLINA STATE UNIVERSITY

( * ) Notice: Subject to any disclaimer, the term of this patent is extended or adjusted under 35 U.S.C. 154(b) by 0 days.

(21) Appl. No.: 15/555,459

(22) PCT Filed: Mar. 4, 2016

(86) PCT No.: PCT/US2016/020825
§ 371 (c)(1),
(2) Date: Sep. 1, 2017

(87) PCT Pub. No.: WO2016/141268
PCT Pub. Date: Sep. 9, 2016

(65) Prior Publication Data
US 2018/0044693 A1 Feb. 15, 2018

Related U.S. Application Data

(60) Provisional application No. 62/128,803, filed on Mar. 5, 2015.

(51) Int. Cl.
*C12N 15/82* (2006.01)
*A01H 1/04* (2006.01)
*C12Q 1/6895* (2018.01)

(52) U.S. Cl.
CPC .......... *C12N 15/8261* (2013.01); *A01H 1/04* (2013.01); *C12N 15/8273* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2013/0067617 A1* 3/2013 Reddy .................. C07K 14/415
800/275
2014/0096445 A1 4/2014 Bassi et al.

OTHER PUBLICATIONS

Yang et al., Environmental and Experimental Botany, 78:157-162; Published 2012.*
Gholipoor et al. (Journal of Agronomy Science, 199(3):155-160; Published Jun. 1, 2013).*
Yang et al. (Environmental and Experimental Botany, 78:157-162, 2012).*
Cooper et al. (Journal of Experimental Botany, 65:6191-6204; Published Mar. 4, 2014).*
Carpita et al., (Trends Plant Sci., 13:415-20; 2008).*
Hatch (Photosynthesis Research; 73:251-256, 2002).*
Jones et al. (TAG, 115(3)361-371; Published May 2007).*
Riar et al. (Experimental and Experimental Botany, 115:58-62; Published Feb. 19, 2015).*
Gholipoor et al., "Transpriration response of maize hybrids to atmospheric vapour pressure deficit", Journal of Agronomy and Crop Science, (2013), 199(3):155-160.
Jones et al., "A comparison of simple sequence repeat and single nucleotide polymorphism marker technologies for the genotypic analysis of maize (*Zea mays* L.)", Theoretical and Applied Genetics, (2007), 115(3):361-371.
Riar et al., "Persistence of limited-transpiration-rate trait in sorghum at high temperature", Environmental and Experimental Botany, (2015), 115:58-62.
Shekoof et al., "Variation Among Maize Hybrids in Response to High Vapor Pressure Deficit at High Temperatures", Crop Science, (2015), 55:392-396.
Yang et al., "Temperature effect on transpiration response of maize plants to vapor pressure deficit", Environmental and Experimental Botany, (2012), 78:157-162.
International Search Report and Written Opinion from the International Searching Authority for PCT/US2016/020825, dated May 17, 2016.
Choudhary et al. "Hydraulic conductance in maize hybrids differing in breakpoint of transpiration response to increasing vapor pressure deficit". Crop Science (2013) 54: 1147-1152.

* cited by examiner

*Primary Examiner* — Vinod Kumar (57) ABSTRACT

Methods to improve drought tolerance and increasing yield by the application limited transpiration trait in maize plants are provided. Expression of the limited transpiration trait in maize under increasing vapor pressure deficit conditions provide positive impact on overall crop yield, depending on environmental conditions.

6 Claims, 7 Drawing Sheets

LIMITED TRANSPIRATION TRAITS AND BREEDING METHODS IN MAIZE

CROSS-REFERENCE

This utility application claims the benefit of priority of U.S. Ser. No. 62/128,803, filed Mar. 5, 2015, which is incorporated herein by reference in its entirety.

FIELD

The field relates to molecular genetics and breeding, particularly with regards to the use of limited transpiration traits for making selections as part of a plant breeding program.

BACKGROUND

Yield loss due to water deficit is ubiquitous in maize (*Zea mays*) production environments in the US Corn Belt, even though it may not be always visually obvious. Stress conditions are associated with soil water deficit and high water demand, and are often manifested in correlations between temperatures and maize yields. In some instances, such as the drought occurring in 2012, the effects of drought can be devastating. Impacts on yield, however, depend on the temporal pattern of water use by the cropping system and physiological response characteristics to developing water deficit of the hybrid. Reduced plant population and skip-row planting systems are common agronomic practices implemented in the western US Corn Belt, which are conducive to increase the proportion of water use during the reproductive phase. Hybrids expressing reduced early growth can provide a complementary path towards soil water conservation and yield increase under drought stress. Similar results could be obtained by using growth retardants applied to limit early season leaf area development and water use.

Limiting transpiration rate under high vapor pressure deficit (VPD) can have a negative impact on yield in some environmental conditions. Decreased stomatal conductance associated with the response to high VPD may also result in decreased carbon assimilation rate. The yield level at which a limitation in dry matter growth (DMg) and transpiration becomes detrimental to yield, the geographies where the trait may limit productivity and their frequency, and how the trait may impact productivity with changes in plant population all remain uncertain.

SUMMARY

Methods to analyze limited transpiration trait and its impact on crop yield are provided herein.

A method to increase maize yield under drought, the method includes selecting a maize plant that expresses a limited transpiration trait under increasing vapor pressure deficit; growing the maize plant under drought and thereby increasing the yield compared to a maize plant not expressing the limited transpiration trait. In an embodiment, the vapor pressure deficit is about 2.0 kPa or higher. In an embodiment, the vapor pressure deficit is about 2-4.0 kPa or higher. In an embodiment, the maize yield is less than about 1300 g/m$^2$. In an embodiment, the maize yield is less than about 1500 g/m$^2$. In an embodiment, the limited transpiration trait is expressed at a temperature of about 38° C. or lower. In an embodiment, the limited transpiration trait response to vapor pressure deficit is lost at about 38° C. or higher. In an embodiment, the limited transpiration trait response to vapor pressure deficit is lost at about 45° C.

A method of breeding a population of maize plants, the method includes selecting a first maize variety that expresses a limited transpiration trait at a first level under increasing vapor pressure deficit; and crossing the first maize plant with a second maize plant that expresses the limited transpiration trait at a second level under increasing vapor pressure deficit. In an embodiment, the first maize variety exhibits a breakpoint at about 2.0 kPa for the limited transpiration trait.

A method of analyzing genotypic variation in a population of maize plants for the expression of a limited transpiration trait, the method includes obtaining the population of maize plants expressing varying levels of the limited transpiration trait; growing the maize plants under high vapor pressure deficit growth conditions; selecting the maize plants that express the limited transpiration trait at a desired environmental condition; and performing genotypic analysis on the selected maize plants. In an embodiment, the environmental condition is selected from the group consisting of grain filling stress, flowering stress and terminal drought.

A method of selecting for the expression of a limited transpiration trait in maize, the method includes (a) correlating yield for a population of maize plants with a parameter selected from the group consisting of environment type, plant density, geographical location, temperature, rainfall, humidity, and radiation; (b) calculating the expression of the limited transpiration trait in maize based on yield and vapor pressure deficit measurements; and (c) selecting the maize plant expressing the limited transpiration trait.

A method of providing a maize plant or seed adapted to drought conditions, the method includes selecting a maize plant or seed that expresses a limited transpiration trait with a breakpoint at about 2.0 kPa or less; associating the expression of the limited transpiration trait with a geographical location or an environmental type characterized as drought-prone; and providing the maize plant or seed adapted to drought conditions.

A method of managing drought stress in a population of maize plants in a crop growing field, the method includes (a) obtaining soil moisture data; (b) obtaining air temperature data; (c) obtaining planting density; (d) processing the soil moisture, temperature and planting density data with expression of the limited transpiration trait of the population of maize plants; and (e) managing drought stress by providing an appropriate level of watering for the population of maize plants in the field.

A method of selecting a transgenic plant expressing a limited transpiration trait, the method includes (a) determining the limited transpiration rate of a population of transgenic plants grown under one or more vapor pressure deficit levels; and (b) selecting the transgenic plant that exhibits the limited transpiration trait at a breakpoint of about 2.0 kPa to about 5.0 kPa. In an embodiment, the transgenic plant expresses the limited transpiration trait at a breakpoint of about 2.0 kPa. In an embodiment, the transgenic plant is maize.

A method of developing a heat stress tolerant maize plant, the method includes (a) selecting a maize plant that exhibits a VPD breakpoint at about 38° C. and (b) growing the maize plant in a crop growing environment wherein daytime growth temperature ranges from about 35° C. to 40° C. In an embodiment, the heat stress tolerant plant is a transgenic plant.

A method of selecting a plant that includes a genetic modification in its genome and expressing a limited transpiration trait, the method includes (a) determining the limited transpiration rate of a population of transgenic plants grown under one or more vapor pressure deficit levels; and (b) selecting the transgenic plant that exhibits the limited transpiration trait at a breakpoint of about 2.0 kPa to about 5.0 kPa.

In an embodiment, the plant expresses the limited transpiration trait at a breakpoint of about 2.0 kPa. In an embodiment, the transgenic plant is maize.

DETAILED DESCRIPTION

The current disclosure provides methods for increasing yield and/or improved performance under drought stress.

Methods to increase maize yield under drought include for example, selecting a maize plant that expresses a limited transpiration trait under increasing vapor pressure deficit; growing the maize plant under drought and thereby increasing the yield compared to a maize plant not expressing the limited transpiration trait. In an embodiment, the vapor pressure deficit (VPD) suitable varies depending the environmental conditions where the plant is grown. In an embodiment, the vapor pressure deficit is about 2.0 kPa or higher. In another embodiment, the vapor pressure deficit is about 2-4.0 kPa or higher. In another embodiment, the VPD is about 3 kPa. Suitable VPDs include for example of about 1.5, 2.0, 2.5, 3.0, 3.5, 4.0, 4.5, 5.0, 5.5, and 6 kPa.

Depending on the environmental conditions and other management practices, the maize yield may vary. In an embodiment, under vapor pressure deficits, the maize yield is less than about 1200 g/m$^2$. In another embodiment, the maize yield is less than about 1500 g/m$^2$. Suitable yield levels for maize include for example, of about 1000 g/m$^2$, 1050 g/m$^2$, 1100 g/m$^2$, 1150 g/m$^2$, 1200 g/m$^2$, 1250 g/m$^2$, 1300 g/m$^2$, 1350 g/m$^2$, 1400 g/m$^2$ and 1500 g/m$^2$.

Depending on the temperature prevailing during the crop growing conditions of the target population of environments, desired level of expression of the limited transpiration trait may vary with the probability of occurrence of heat stress. For example, in an embodiment, under temperatures of about 38° C. or higher, loss of expression of the limited-transpiration trait may be suitable. In other embodiments, temperature ranges from about 25° C. to about 45° C. may be suitable. Suitable temperatures include for example, 30° C., 31° C., 32° C., 33° C., 34° C., 35° C., 36° C., 37° C., 38° C., 39° C., 40° C., 41° C., 42° C., 43° C., 44° C. and 45° C.

Resistance to heat stress by crop plants such as maize indicate the ability to withstand increased minimal and maximal day/night temperatures and in particular increased minimal temperatures. The ability to withstand heat stress may be in the form of reduced yield loss. Conditions of heat stress include for example, minimal night temperatures of 22° C. or above, 23° C. or above, 24° C. or above, 25° C. or above, 26° C. or above, 27° C. or above, 28° C. or above, 29° C. or above, and 30° C. or above. In an embodiment, crop plants are affected by heat stress during the reproductive phases of growth of the plant, e.g., flowering stage and grain filling stage in maize.

Methods of breeding a population of maize plants include for example, selecting a first maize variety that expresses a limited transpiration trait at a first level under increasing vapor pressure deficit; and crossing the first maize plant with a second maize plant that expresses the limited transpiration trait at a second level under increasing vapor pressure deficit. In an embodiment, the first level limited transpiration trait may have a higher VPD breakpoint than the plant expressing the limited transpiration trait at a second level. In another embodiment, the first and second levels of the limited transpiration trait refer to the varying levels of the limited transpiration trait expressed by two or more populations of the maize plants at varying VPD levels. In an embodiment, the maize plants may include a transgene to modulate the limited transpiration trait. Suitable VPDs for the maize plants include for example of about 1.5, 2.0, 2.5, 3.0, 3.5, 4.0, 4.5, 5.0, 5.5, and 6 kPa or higher.

In an embodiment, suitable VPD breakpoints include for example. The method of claim 6, wherein the first maize variety exhibits a breakpoint of about 1.5, 2.0, 2.5, 3.0, 3.5, 4.0, 4.5, 5.0, 5.5, and 6 kPa for the limited transpiration trait.

In an embodiment, methods of analyzing genotypic variation in a population of maize plants for the expression of a limited transpiration trait includes for example, the method comprising obtaining the population of maize plants expressing varying levels of the limited transpiration trait; growing the maize plants under high or increased vapor pressure deficit growth conditions; selecting the maize plants that express the limited transpiration trait at a desired environmental condition; and performing genotypic analysis on the selected maize plants. In an embodiment, the environmental condition is selected from the group consisting of grain filling stress, flowering stress and terminal drought. Genotypic variations include for example, QTL, polymorphisms including SNP markers, haplotype variations, transgenes, mutations, and any other variation in the genome.

In an embodiment, methods of selecting for the expression of a limited transpiration trait in maize include for example (a) correlating yield for a population of maize plants with a parameter selected from the group consisting of environment type, plant density, geographical location, temperature, rainfall, humidity, and radiation; (b) calculating the expression of the limited transpiration trait in maize based on yield and vapor pressure deficit measurements; and (c) selecting the maize plant expressing the limited transpiration trait. Other parameters include for example, soil moisture, soil conditions, plant maturity, management practices including watering, fertilizer application, pest management, and any germplasm by environment interaction.

In an embodiment, methods of providing a maize plant or seed adapted to drought conditions, the methods include selecting a maize plant or seed that expresses a limited transpiration trait with a breakpoint at about 2.0 kPa or less or about 1.5, 2.0, 2.5, 3.0, 3.5, 4.0, 4.5, 5.0, 5.5, and 6 kPa; associating the expression of the limited transpiration trait with a geographical location or an environmental type characterized as drought-prone; and providing the maize plant or seed adapted to drought conditions. Determination of the limited transpiration trait at one or more target VPD levels are performed using methods disclosed herein. Drought conditions can be determined by a variety of methods including for example, soil moisture probes, air temperature, humidity measurements, historical VPD calculations, remote sensing data and any other direct or indirect measurements.

In an embodiment, methods of managing drought stress in a population of maize plants in a crop growing field, the methods include for example, (a) obtaining soil moisture data; (b) obtaining air temperature data; (c) obtaining planting density; (d) processing the soil moisture, temperature and planting density data with expression of the limited transpiration trait of the population of maize plants; and (e) managing drought stress by providing an appropriate level of watering for the population of maize plants in the field. In an embodiment, the timing of the watering is determined based on the expression of the limited transpiration trait and the existing VPD conditions.

In an embodiment, methods of selecting a transgenic plant expressing a limited transpiration trait, the method comprising (a) determining the limited transpiration rate of a population of transgenic plants grown under one or more vapor pressure deficit levels; and (b) selecting the transgenic plant that exhibits the limited transpiration trait at a breakpoint of about 2.0 kPa to about 5.0 kPa. Depending on the environmental conditions, maize plants with varying transpiration rate breakpoints may be selected. For example, a transgenic maize plant having a VPD breakpoint of about 3.5 kPa or higher may be selected for those geographical regions that typically experience higher VPDs compared to a region having a lower VPD, such as for example of about 2.0 kPa or lower.

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein, the term "allele" refers to a variant or an alternative sequence form at a genetic locus. In diploids, single alleles are inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the phrase "associated with" refers to a recognizable and/or assayable relationship between two entities. For example, the phrase "associated with a trait" refers to a locus, gene, allele, marker, phenotype, etc., or the expression thereof, the presence or absence of which can influence an extent, degree, and/or rate at which the trait is expressed in an individual or a plurality of individuals.

As used herein, the term "backcross", and grammatical variants thereof, refers to a process in which a breeder crosses a progeny individual back to one of its parents: for example, a first generation $F_1$ with one of the parental genotypes of the $F_1$ individual.

As used herein, the phrase "breeding population" refers to a collection of individuals from which potential breeding individuals and pairs are selected. A breeding population can be a segregating population.

A "candidate set" is a set of individuals that are genotyped at marker loci used for genomic prediction. The candidates may be hybrids.

As used herein, the term "chromosome" is used in its art-recognized meaning as a self-replicating genetic structure containing genomic DNA and bearing in its nucleotide sequence a linear array of genes.

As used herein, the terms "cultivar" and "variety" refer to a group of similar plants that by structural and/or genetic features and/or performance can be distinguished from other members of the same species.

The term "limited transpiration trait" refers to the expression of a trait that limits further increase in transpiration rate under certain environmental conditions such as for example, high vapor pressure deficit (VPD) conditions.

The term "VPD" generally refers to the difference/deficit between the amount of moisture in the air/atmosphere and how much moisture the air can hold when it is saturated. In general terms, as the VPD increases, to maintain the plant water status, transpiration and carbon assimilation that support growth and yield, the plant's need to extract more water from the soil through its roots increases. With respect to the plants, the VPD may also relate to the difference between the vapor pressure inside the leaf compared to the vapor pressure of the air. In other words, VPD may also be characterized as the atmospheric demand for water or the 'drying power' of the air. VPD is usually measured in pressure units such as millibars or kilopascals. VPD unit is simply a measure of relative humidity at a given temperature as a single value and is inversely proportion to relative humidity (RH): VPD is low when RH is high and vice versa.

The term "VPD breakpoint" indicates the VPD beyond which the transpiration rate increase is no longer linear. Depending on the nature and expression of the limited transpiration trait, the VPD breakpoint may occur at a specific VPD (e.g., 2.5 kPa) or the breakpoint may occur within a range of VPD (e.g., between 2.5 and 3.0 kPa).

The term "canopy conductance", denoted $g_c$, refers to the ratio of water use to mean vapor pressure deficit (VPD). In an embodiment, ratio of daily or other time step water use to daily mean VPD is presented as the canopy conductance.

The term "stomatal conductance" refers to the measure of the rate of passage of carbon dioxide ($CO_2$) entering, or water vapor exiting through the stomata of a leaf, usually measured in mmol $m^{-2}$ $s^{-1}$.

Because of the relationship between transpiration and VPD, leaf and/or canopy conductance can be utilized to characterize maize inbreds and hybrids for the limited transpiration rate.

As used herein, the phrase "determining the genotype" or "analyzing genotypic variation" or "genotypic analysis" of an individual refers to determining at least a portion of the genetic makeup of an individual and particularly can refer to determining genetic variability in an individual that can be used as an indicator or predictor of a corresponding phenotype. Determining a genotype can comprise determining one or more haplotypes or determining one or more polymorphisms exhibiting linkage disequilibrium to at least one polymorphism or haplotype having genotypic value. Determining the genotype of an individual can also comprise identifying at least one polymorphism of at least one gene and/or at one locus; identifying at least one haplotype of at least one gene and/or at least one locus; or identifying at least one polymorphism unique to at least one haplotype of at least one gene and/or at least one locus. Genotypic variations may also include inserted transgenes or other changes engineered in the host genome.

A "doubled haploid plant" is a plant that is developed by the doubling of a haploid set of chromosomes. A doubled haploid plant is homozygous.

As used herein, the phrase "elite line" refers to any line that is substantially homozygous and has resulted from breeding and selection for superior agronomic performance.

As used herein, the term "gene" refers to a hereditary unit including a sequence of DNA that occupies a specific location on a chromosome and that contains genetic instructions for a particular characteristic or trait in an organism. As used herein, the phrase "genetic gain" refers to an amount of an increase in performance that is achieved through artificial genetic improvement programs. The term "genetic gain" can refer to an increase in performance that is achieved after one generation has passed.

As used herein, the phrase "genetic map" refers to an ordered listing of loci usually related to the relative positions of the loci on a particular chromosome.

As used herein, the phrase "genetic marker" refers to a nucleic acid sequence (e.g., a polymorphic nucleic acid sequence) that has been identified as being associated with a trait, locus, and/or allele of interest and that is indicative of and/or that can be employed to ascertain the presence or absence of the trait, locus, and/or allele of interest in a cell or organism. Examples of genetic markers include, but are not limited to genes, DNA or RNA-derived sequences (e.g., chromosomal subsequences that are specific for particular sites on a given chromosome), promoters, any untranslated regions of a gene, microRNAs, short inhibitory RNAs (siRNAs; also called small inhibitory RNAs), quantitative trait loci (QTLs), transgenes, mRNAs, double-stranded RNAs, transcriptional profiles, and methylation patterns.

As used herein, the term "genotype" refers to the genetic makeup of an organism. Expression of a genotype can give rise to an organism's phenotype (i.e., an organism's observable traits). A subject's genotype, when compared to a reference genotype or the genotype of one or more other subjects, can provide valuable information related to current or predictive phenotypes. The term "genotype" thus refers to the genetic component of a phenotype of interest, a plurality of phenotypes of interest, and/or an entire cell or organism.

As used herein, "haplotype" refers to the collective characteristic or characteristics of a number of closely linked loci within a particular gene or group of genes, which can be inherited as a unit. For example, in some embodiments, a haplotype can comprise a group of closely related polymorphisms (e.g., single nucleotide polymorphisms; SNPs). A haplotype can also be a characterization of a plurality of loci on a single chromosome (or a region thereof) of a pair of homologous chromosomes, wherein the characterization is indicative of what loci and/or alleles are present on the single chromosome (or the region thereof).

As used herein, the term "heterozygous" refers to a genetic condition that exists in a cell or an organism when different alleles reside at corresponding loci on homologous chromosomes.

As used herein, the term "homozygous" refers to a genetic condition existing when identical alleles reside at corresponding loci on homologous chromosomes. It is noted that both of these terms can refer to single nucleotide positions, multiple nucleotide positions (whether contiguous or not), and/or entire loci on homologous chromosomes.

As used herein, the term "hybrid", when used in the context of a plant, refers to a seed and the plant the seed develops into that results from crossing at least two genetically different plant parents.

As used herein, the term "inbred" refers to a substantially or completely homozygous individual or line. It is noted that the term can refer to individuals or lines that are substantially or completely homozygous throughout their entire genomes or that are substantially or completely homozygous with respect to subsequences of their genomes that are of particular interest.

As used herein, the term "introgress", and grammatical variants thereof (including, but not limited to "introgression", "introgressed", and "introgressing"), refer to both natural and artificial processes whereby one or more genomic regions of one individual are moved into the genome of another individual to create germplasm that has a new combination of genetic loci, haplotypes, and/or alleles. Methods for introgressing a trait of interest can include, but are not limited to, breeding an individual that has the trait of interest to an individual that does not and backcrossing an individual that has the trait of interest to a recurrent parent.

As used herein, "linkage disequilibrium" (LD) refers to a derived statistical measure of the strength of the association or co-occurrence of two distinct genetic markers. Various statistical methods can be used to summarize LD between two markers but in practice only two, termed D' and $r^2$, are widely used (see e.g., Devlin & Risch 1995; Jorde, 2000). As such, the phrase "linkage disequilibrium" refers to a change from the expected relative frequency of gamete types in a population of many individuals in a single generation such that two or more loci act as genetically linked loci.

As used herein, the phrase "linkage group" refers to all of the genes or genetic traits that are located on the same chromosome. Within a linkage group, those loci that are sufficiently close together physically can exhibit linkage in genetic crosses. Since the probability of a crossover occurring between two loci increases with the physical distance between the two loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region (i.e., less than the entirety) of a given chromosome.

As used herein, the term "locus" refers to a position on a chromosome of a species, and can encompass a single nucleotide, several nucleotides, or more than several nucleotides in a particular genomic region.

As used herein, the terms "marker" and "molecular marker" are used interchangeably to refer to an identifiable position on a chromosome the inheritance of which can be monitored and/or a reagent that is used in methods for visualizing differences in nucleic acid sequences present at such identifiable positions on chromosomes. A marker can comprise a known or detectable nucleic acid sequence. Examples of markers include, but are not limited to genetic markers, protein composition, peptide levels, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency, energy yield, secondary compounds, metabolites, morphological characteristics, and agronomic characteristics. Molecular markers include, but are not limited to restriction fragment length polymorphisms (RFLPs), random amplified polymorphic DNA (RAPD), amplified fragment length polymorphisms (AFLPs), single strand conformation polymorphism (SSCPs), single nucleotide polymorphisms (SNPs), insertion/deletion mutations (indels), simple sequence repeats (SSRs), microsatellite repeats, sequence-characterized amplified regions (SCARs), cleaved amplified polymorphic sequence (CAPS) markers, and isozyme markers, microarray-based technologies, TAQMAN® markers, ILLUMINA® GOLDENGATE® Assay markers, nucleic acid sequences, or combinations of the markers described herein, which can be employed to define a specific genetic and/or chromosomal location.

A marker may correspond to an amplification product generated by amplifying a nucleic acid with one or more oligonucleotides, for example, by the polymerase chain reaction (PCR). As used herein, the phrase "corresponds to an amplification product" in the context of a marker refers to a marker that has a nucleotide sequence that is the same as or the reverse complement of (allowing for mutations introduced by the amplification reaction itself and/or naturally occurring and/or artificial alleleic differences) an amplification product that is generated by amplifying a nucleic acid with a particular set of oligonucleotides. In some embodiments, the amplifying is by PCR, and the oligonucleotides are PCR primers that are designed to hybridize to opposite strands of a genomic DNA molecule in order to amplify a genomic DNA sequence present between the sequences to which the PCR primers hybridize in the genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

The term "phenotype" refers to any observable property of an organism, produced by the interaction of the genotype of the organism and the environment. A phenotype can encompass variable expressivity and penetrance of the phenotype. Exemplary phenotypes include but are not limited to a visible phenotype, a physiological phenotype, a susceptibility phenotype, a cellular phenotype, a molecular phenotype, and combinations thereof.

As used herein, the term "plant" refers to an entire plant, its organs (i.e., leaves, stems, roots, flowers etc.), seeds, plant cells, and progeny of the same. The term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "polymorphism" refers to the presence of one or more variations of a nucleic acid sequence at a locus in a population of one or more individuals. The sequence variation can be a base or bases that are different, inserted, or deleted. Polymorphisms can be, for example, single nucleotide polymorphisms (SNPs), simple sequence repeats (SSRs), and Indels, which are insertions and deletions. Additionally, the variation can be in a transcriptional profile or a methylation pattern. The polymorphic sites of a nucleic acid sequence can be determined by comparing the nucleic acid sequences at one or more loci in two or more germplasm entries. As such, in some embodiments the term "polymorphism" refers to the occurrence of two or more genetically determined alternative variant sequences (i.e., alleles) in a population. A polymorphic marker is the locus at which divergence occurs. Exemplary markers have at least two (or in some embodiments more) alleles, each occurring at a frequency of greater than 1%. A polymorphic locus can be as small as one base pair (e.g., a single nucleotide polymorphism; SNP).

As used herein, the term "population" refers to a genetically heterogeneous collection of plants that in some embodiments share a common genetic derivation.

As used herein, the term "progeny" refers to any plant that results from a natural or assisted breeding of one or more plants. For example, progeny plants can be generated by crossing two plants (including, but not limited to crossing two unrelated plants, backcrossing a plant to a parental plant, intercrossing two plants, etc.), but can also be generated by selfing a plant, creating an inbred (e.g., a double haploid), or other techniques that would be known to one of ordinary skill in the art. As such, a "progeny plant" can be any plant resulting as progeny from a vegetative or sexual reproduction from one or more parent plants or descendants thereof. For instance, a progeny plant can be obtained by cloning or selfing of a parent plant or by crossing two parental plants and include self ings as well as the $F_1$ or $F_2$ or still further generations. An $F_1$ is a first-generation progeny produced from parents at least one of which is used for the first time as donor of a trait, while progeny of second generation ($F_2$) or subsequent generations ($F_3$, $F_4$, and the like) are in some embodiments specimens produced from self ings (including, but not limited to double haploidization), intercrosses, backcrosses, or other crosses of $F_1$ individuals, $F_2$ individuals, and the like. An $F_1$ can thus be (and in some embodiments, is) a hybrid resulting from a cross between two true breeding parents (i.e., parents that are true-breeding are each homozygous for a trait of interest or an allele thereof, and in some embodiments, are inbred), while an $F_2$ can be (and in some embodiments, is) a progeny resulting from self-pollination of the $F_1$ hybrids.

As used herein, the phrase "single nucleotide polymorphism", or "SNP", refers to a polymorphism that constitutes a single base pair difference between two nucleotide sequences. As used herein, the term "SNP" also refers to differences between two nucleotide sequences that result from simple alterations of one sequence in view of the other that occurs at a single site in the sequence. For example, the term "SNP" is intended to refer not just to sequences that differ in a single nucleotide as a result of a nucleic acid substitution in one as compared to the other, but is also intended to refer to sequences that differ in 1, 2, 3, or more nucleotides as a result of a deletion of 1, 2, 3, or more nucleotides at a single site in one of the sequences as compared to the other. It would be understood that in the case of two sequences that differ from each other only by virtue of a deletion of 1, 2, 3, or more nucleotides at a single site in one of the sequences as compared to the other, this same scenario can be considered an addition of 1, 2, 3, or more nucleotides at a single site in one of the sequences as compared to the other, depending on which of the two sequences is considered the reference sequence. Single site insertions and/or deletions are thus also considered to be encompassed by the term "SNP".

As used herein, the terms "trait" and "trait of interest" refer to a phenotype of interest, a gene that contributes to a phenotype of interest, as well as a nucleic acid sequence associated with a gene that contributes to a phenotype of interest. Any trait that would be desirable to screen for or against in subsequent generations can be a trait of interest. Exemplary, non-limiting traits of interest include yield, disease resistance, agronomic traits, abiotic traits, kernel composition (including, but not limited to protein, oil, and/or starch composition), insect resistance, fertility, silage, and morphological traits. In some embodiments, two or more traits of interest are screened for and/or against (either individually or collectively) in progeny individuals.

EXAMPLES

The present disclosure is further illustrated in the following Examples. It should be understood that these Examples, while indicating embodiments of the invention, are given by way of illustration only. Thus, various modifications to the crop model, the relationships to simulate/model the limited transpiration trait, methods of analyses, and applying such methods for crop improvement are disclosed.

Example 1

Models and Methodologies

A mechanistic model was used to conduct simulation experiments (Muchow and Sinclair (1991), Agronomy Journal 83, 1052-1059; Muchow et al., (1990), Agronomy Journal 82, 338-343.). Given the structure of the model it is referred here as a simple simulation model (SSM). The SSM model proved to reasonably reproduce field experiments and it was used in simulation studies in the United States previously.

The SSM model was developed using the concept of resource capture, resource use efficiency and partitioning of mass to grain. Crop and canopy development are determined as a function of temperature. Growth is modeled as a function of light interception and radiation use efficiency, which was set to 1.85 g $MJ^{-1}$ (Hammer et al., (2009), Crop Science 49, 299-312). Grain yield is simulated based on the linear increase of harvest index during seed fill. Simulated yield is calculated on a dry matter basis and adjusted to 15.5% moisture content. Both canopy expansion and growth are dependent on soil water content, with effects modeled as a function of the fraction of transpirable soil water (FTSW). Transpiration is calculated from growth and atmospheric VPD, using a transpiration efficiency coefficient for maize of 9 Pa.

(A) Implementing the Limited-Transpiration Trait in SSM

Figure 1:
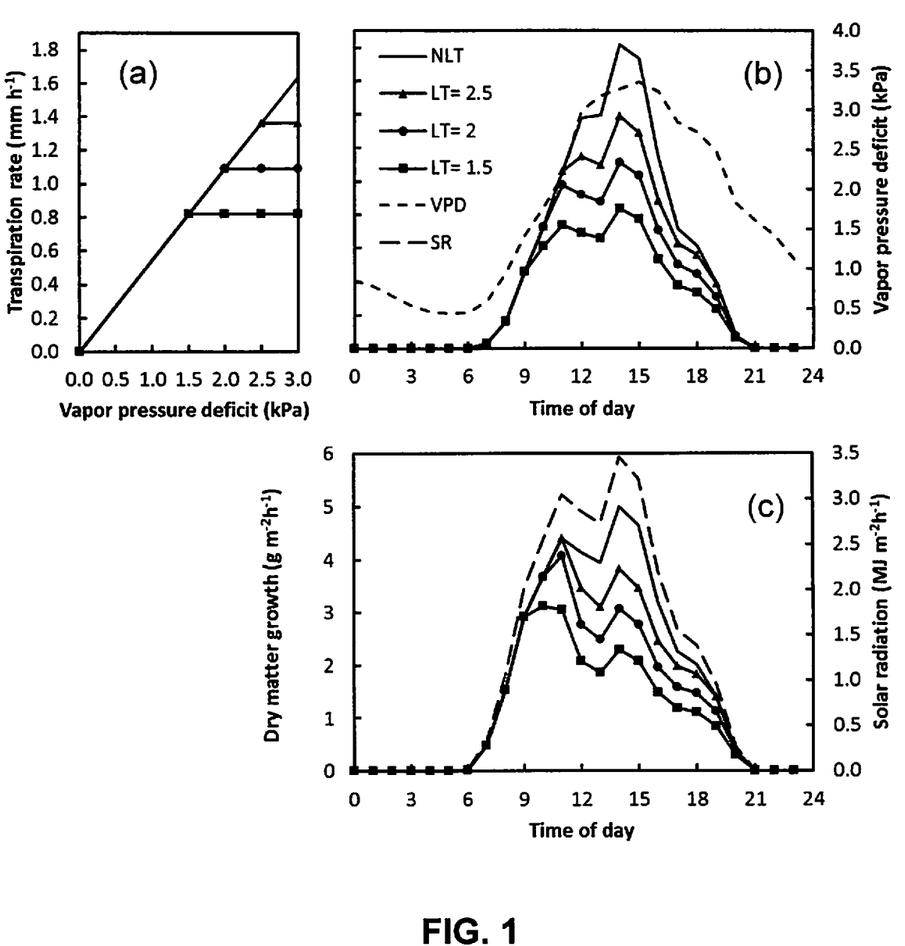
FIG. 1 shows transpiration rate (mm hr-1) response to vapor pressure deficit (VPD, kPa) calculated for three hybrids expressing the limited-transpiration trait as determined by changes in transpiration response to vapor pressure deficit breakpoint (LT) and a reference hybrid not expressing any limitation (NLT) assuming leaf area index equal to 4, coefficient of light extinction equal to 0.38 and radiation use efficiency equal to 1.85 g MJ-1 (a). Hourly measured vapor pressure deficit and solar radiation (SR) in St. Johns, Kans. on 10 Jul. 2012 and corresponding calculated transpiration rates (b) and dry matter growth (c) for the reference hybrid and three hybrids expressing the limited-transpiration trait.

Since the limited-transpiration trait restricted transpiration rate during periods of high VPD during the day, it was necessary to modify the SSM model to calculate transpiration rate on hourly time steps rather than daily time steps. This change required that the daily weather input be interpolated for hourly time steps. A simple function was introduced such that when VPD at any hourly time step exceeded a threshold $VPD_0$ water loss was held to the rate calculated for a vapor pressure deficit at the threshold (FIG. 1a). Therefore, transpiration for a genotype expressing the trait is less than for a genotype not expressing the trait when VPD is greater than $VPD_0$ (FIG. 1b). The consequence of this behavior in the model is soil water conservation, with the magnitude depending on the frequency and size of the difference between VPD and $VPD_0$. The decrease in transpiration rate at high VPD was also imposed on the calculation of hourly mass accumulation by the crop resulting in decreased crop growth (FIG. 1c). The resulting effects on soil water use are manifested in the value of FTSW that determines the level of stress on leaf expansion and growth under drought conditions.

(B) Simulation Studies

The U.S. maize production region, defined as the region where the area sown with maize is greater than 2023 hectares within a 30 km×30 km grid cell, was divided into 2603 individual geographical units. Sowing date, plant population, hybrid maturity, and available soil water were assigned to each grid. Hybrid maturity was set to vary from relative maturity of 95 to 123 depending on location using the method described by Löffler (Löffler et al., (2005), Crop Science 45, 1708-1716) (the environment classification methods, incorporated herein by reference). Total soil water holding capacity was determined using soil depth from the STATSGO database (United States Department of Agriculture, 2015. Soil survey staff, Natural Resources Conservation Service, United States Department of Agriculture and a constant (0.13 cm3 cm-3) volumetric fraction of available soil water (Muchow and Sinclair, 1991. Agron. J. 83:1052-1059). Digital General Soil Map of the United States or STATSGO is a broad-based inventory of soils and non-soil areas that are present in a repeatable pattern on the landscape and that can be cartographically shown. A scenario of soil moisture initial conditions was constructed using public data from the U.S. Climate Reference Network and the National Oceanic and Atmospheric Administration (NOAA; Bell et al., 2013. J. Hydrometeorol. 14:977-988.) Time series of daily minimum and maximum temperature and precipitation data for each grid cover the period 1950-2012. Hourly temperature, from which VPD was calculated, was modeled from minimum and maximum temperature by assuming a harmonic change in the temperature cycle on each day. Hourly solar radiation was calculated assuming a sinusoidal change in incident radiation during daylight hours and the daily integral was estimated from temperature records using parameters provided by commercial vendor Mud Springs Geographers, Inc. (Temple, Tex.). The model was run independently for each season and grid for a total of 163,989 environments (63 seasons×2603 grids).

The base plant population ranged from 8 to 6 plants m$^{-2}$ in an east-west gradient. Two additional populations were simulated for each environment by multiplying the base plant population for the grid by 0.75 and 1.25. In addition, three putative hybrids with differing VPD thresholds were explored. One hybrid not expressing the limited transpiration trait was set as a reference. VPD breakpoints were set to 1.5, 2.0 and 2.5 kPa.

(C) Analyses and Assessment

Considering the limited-transpiration rate restricts growth there are theoretical limits to potential yield. Regressing yield for each grid and year combination against simulated yield for the control hybrid provides a quantitative assessment of the sensitivity of the trait and enables calculating the yield level at which the trait benefit equals zero ($Y_0$).

Spatial distributions of the limited-transpiration trait impact on yield were determined by calculating the first, second and third quartile for the yield difference between the putative limited transpiration hybrid and the reference hybrid (YD). These quartiles represent wet (first), normal (second), and dry (third) seasons, herein $YD_{25}$, $YD_{50}$, and $YD_{75}$. Positive values indicate yield gain and negative values indicate yield loss due to the trait modification.

To quantify sources of variation associated with hybrid (H), environment type (E), and management (M), and their interactions, the simulated yield data were analyzed using a fixed effect model, $$Y_{ljM}=u+H_l+E_j+M_k+(HE)_{ij}+(HM)_{lk}+(EM)_{jk}+(HEM)_{ijk}+B_{ijkl}$$

where the simulated yield ($Y_{ljM}$) of hybrid l in management k, within environment (year-location combination), within environment type j was modeled as a function of an overall mean u, factors for hybrid environment type l, and management k, two-way interactions between hybrid, environment type, and management, the three-way interaction between them, and the residual $B_{ijkl}$. An F test was used to assess significance for fixed effects. Analyses were conducted with ASREML (Gilmour (2009), ASRemI User Guide Release 3.0 VSN International Ltd, Hemel Hempstead, HP1 1ES, UK).

The methods described by Chapman (Chapman et al., (2000), Australian Journal of Agricultural Research 51, 209-222) were adapted to characterize environments for the type of stress pattern. In this work, drought-stress patterns were determined by the temporal trajectories of FTSW rather than on relative transpiration, and the temporal series of FTSW were centered at anthesis date. Cluster analysis was conducted by applying the k-means algorithm to the FTSW time series for the control hybrid. The complete set of 163,989 environments that result from the combination of year and location (grid) was summarized by grouping the individual environments in groups of "Environment-types" characterized by the average stress pattern.

Example 2

Stimulated Yields Using the Standard Model

Figure 2:
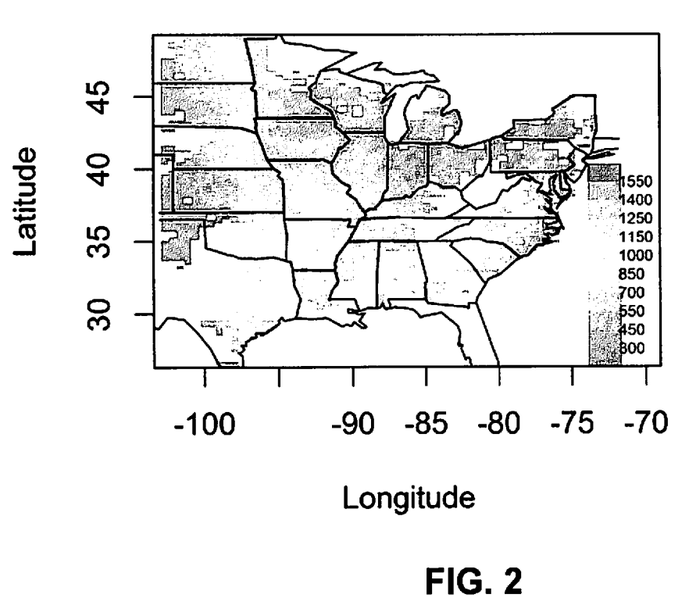
FIG. 2 shows spatial distribution of mean simulated yields (g m$^{-2}$) over 63 years (1950-2012) in the maize producing regions in the U.S. for the reference hybrid not expressing the limited-transpiration trait.

Average simulated yields for control runs, i.e. hybrids not expressing the limited transpiration trait, show wide spatial variation (FIG. 2). Highest values were simulated for the Central-Eastern US Corn Belt with average yields in the range of 1000-1600 g m–2. The locations of highest yield conform well to the areas where maize is a dominant crop of maize. A steep reduction in yield from 1200 to 200 g m–2 was simulated west of longitude 95° W, consistent with an East-West precipitation gradient and soil moisture at sowing. Simulated yields were also reduced relative to those simulated for the Central Corn Belt for most of the state of Missouri and the South-East US. Yield reductions from those attained in the Central Corn Belt are widespread and enable the possibility to identify regions where the limited-transpiration rate trait can have a positive influence on yield.

Example 3

Value of Limited-Transpiration Trait Increase with Decreasing $VPD_0$

Figure 3:
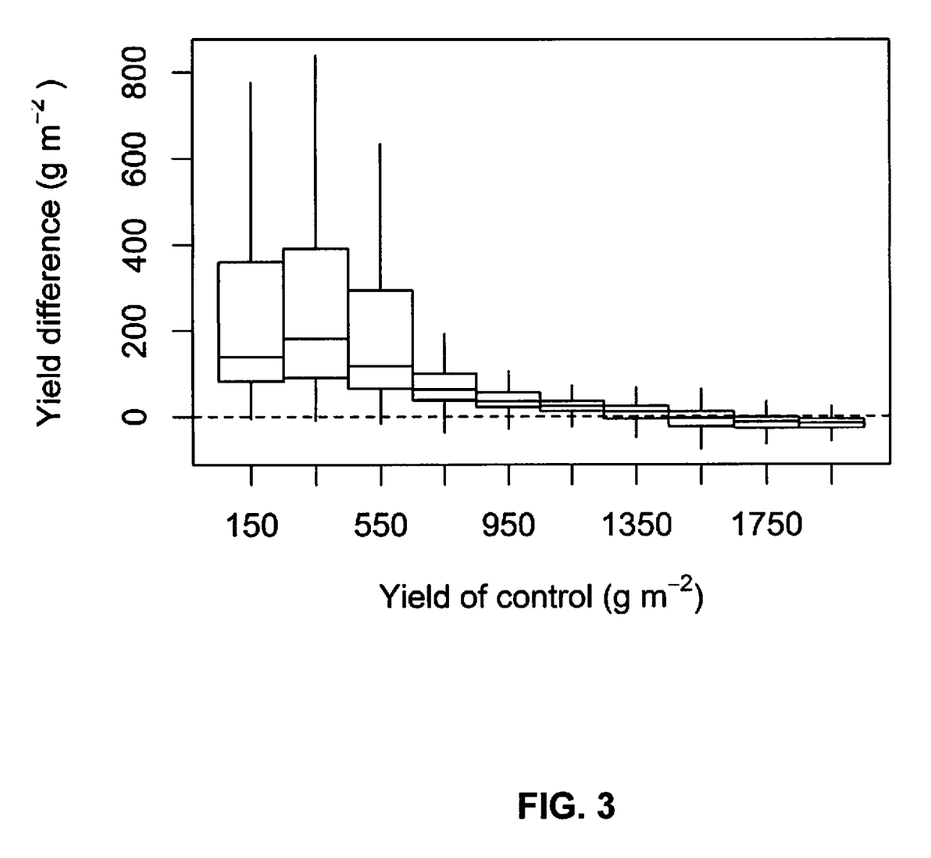
FIG. 3 shows a boxplot of simulated yield (g m–2) difference associated with change in transpiration response to limited (vapor pressure deficit breakpoint 2 kPa) from non-limited reference hybrid versus simulated yield level of the reference. Boxplot shows first and third quartile, and median. Boxplot whiskers extend 1.5 times the interquartile range out from the box.

The yield difference between a hybrid with breakpoint $VPD_0$ of 2 kPa and the reference hybrid not expressing a breakpoint is presented for each location and year in FIG. 3. Simulated yields for the hybrid expressing the limited-transpiration trait are consistently positive for yield levels lower than 750 g m$^{-2}$. There are increasing yield penalties with increasing frequency as yield levels increased beyond at about 1150 g m$^{-2}$. Using regression analyses (y=242±0.6–0.17±0.0005·x; r$^2$=0.42) the yield level at which the average yield difference is zero for $VPD_0$ equal to 2 kPa, was estimated at 1382 g m$^{-2}$. This point of indifference increases to 1416 g m$^{-2}$ when $VPD_0$ was set at 2.5 kPa (y=127±0.5–0.09±0.0004·x; r$^2$=0.23) and decreases to 1235 g m$^{-2}$ when $VPD_0$ was 1.5 kPa (y=375±0.67–0.30±0.0006·x; r$^2$=0.63). The level of expression of the trait determines the degree of limitation of transpiration and growth (FIG. 1), and consequently the tradeoff between yield improvement in lower yielding environments and the yield penalty in favorable conditions.

Example 4

Regional Patterns of the Value of the Limited-Transpiration Trait

Figure 4:
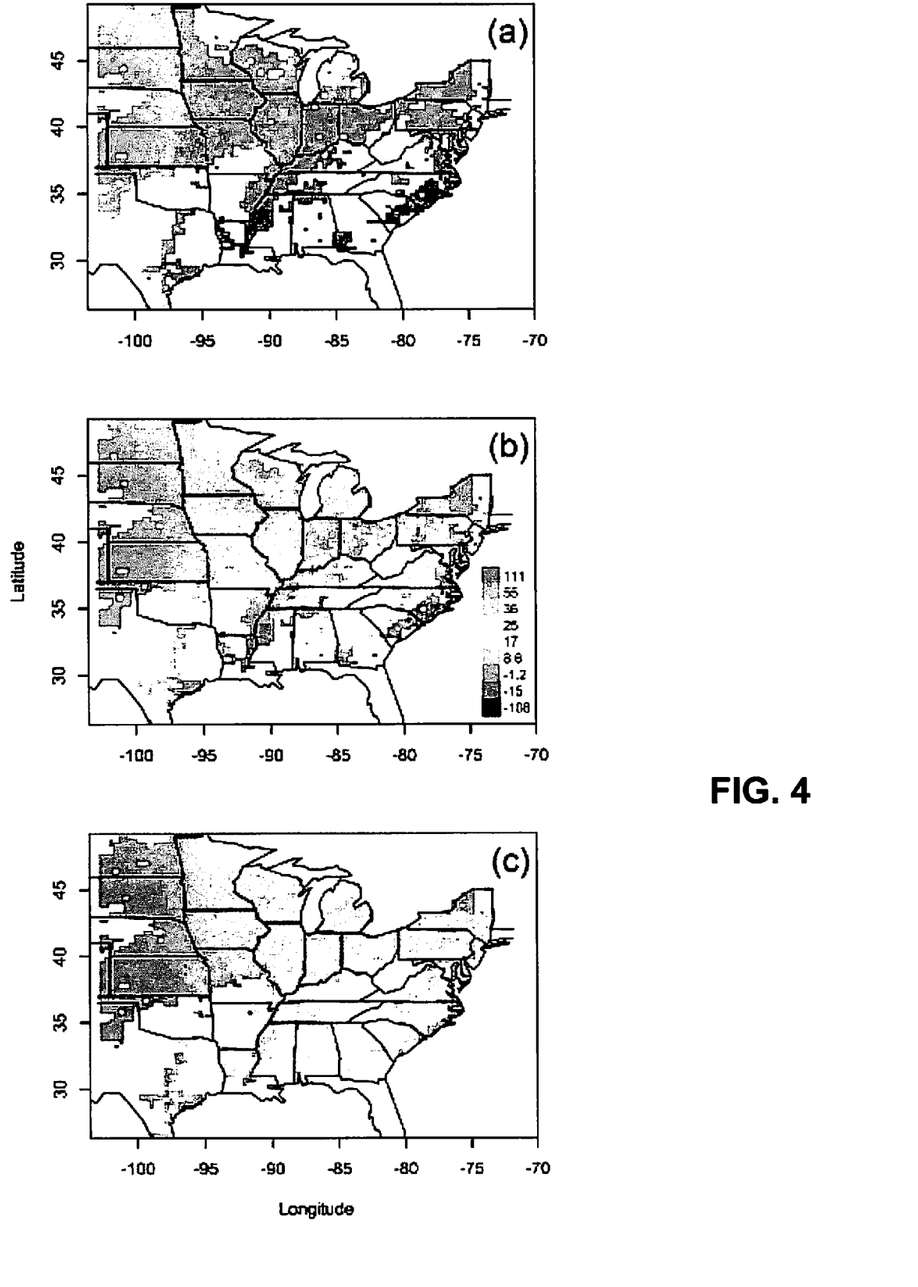
FIG. 4 shows spatial distributions of simulated yield difference (g m$^{-2}$) associated with change in transpiration response to limited (vapor pressure deficit breakpoint 2 kPa) from non-limited reference with exceedance probability of 25% (a), 50% (b) and 75% (c)

Spatial and temporal patterns of yield response to expression of the breakpoint in transpiration response to VPD were studied for a hybrid with $VPD_0$ of 2 kPa as compared to the reference hybrid not expressing any limitation. Three regions corresponding approximately to the Western (West of longitude 95° W), Central-East (North of latitude 37° N), and Mississippi delta and U.S. Coastal Plains could be identified by comparing $YD_{25}$, $YD_{50}$, and $YD_{75}$ maps (FIG. 4). Yield gains in the Western Corn Belt were greater than zero in at least 75% of the years with median yield gains ($YD_{50}$) ranging from 10 to 50 g m$^{-2}$. In contrast, yield penalties were clearly observable in the other two regions. $YD_{50}$ varied from positive (9.0 g m$^{-2}$) to negative (−15 g m$^{-2}$) in the Mississippi delta and U.S. Coastal Plains while it varied around zero (−15 to 25 g m$^{-2}$) in the Central-East Corn-Belt. A noteworthy characteristic of both the Central-East and the Mississippi delta and U.S. Coastal Plainsis the large oscillation from negative to positive benefits from expression of the limited-transpiration trait. In years with higher rainfall, yield penalty as estimated by $YD_{25}$ was around −50 g m$^{-2}$ and consistently distributed throughout the regions. While in environments with lower rainfall, yield gains as estimated by $YD_{75}$ were in the order of 25 g m$^{-2}$ Example 5

Figure 5:
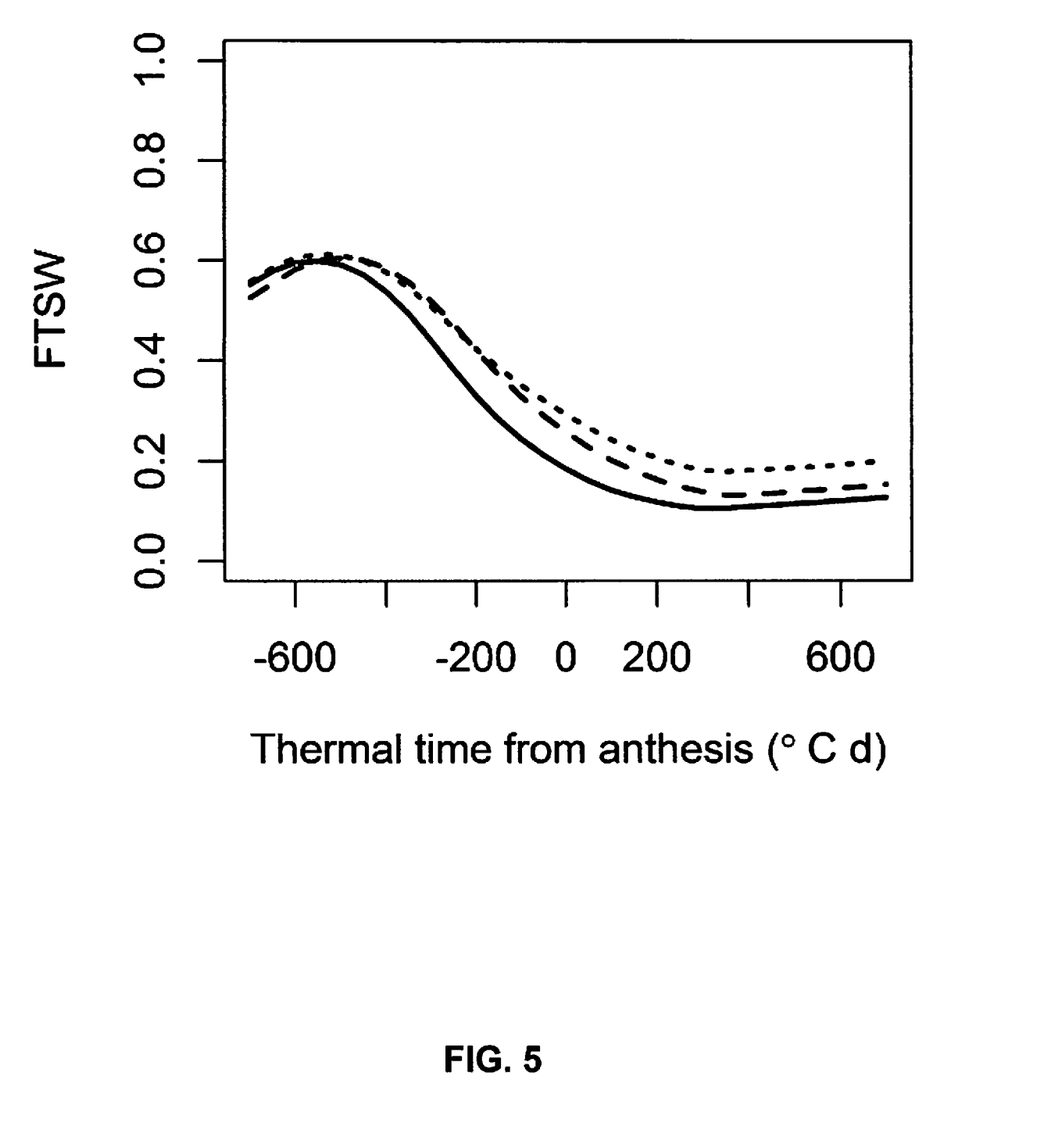
FIG. 5 shows the average temporal dynamics of fraction of transpirable soil water (FTSW) for three hypothetical genotypes that differ in the transpiration response to vapor pressure deficit: unlimited (solid line), breakpoint equal to 2 kPa (broken line), and breakpoint equal to 1.5 kPa (dotted line). Average calculated for all grids and years classified either as environment type flowering and grain fill stress, or terminal drought stress. Thermal time (° C.) as the average between daily maximum and minimum temperature with base temperature for preflowering equal to 8° C. and postflowering equal to 0° C.

Value of the Limited-Transpiration Trait is Associated with Dynamics of Water Use FIG. 5 shows the average temporal dynamics of the fraction of transpirable soil water for three hybrids expressing a $VPD_0$ breakpoint at 1.5 and 2.0 kPa and a reference hybrid not expressing the trait. Means were calculated across years and grids that were classified either as environment type flowering and grain fill stress or terminal drought stressFig. The reduction in transpiration rate during periods of high VPD resulted in an observable increase, although not large, in the soil water balance starting around 400° C. after sowing. The magnitude of the shift relative to the non-limited reference was greater for the hybrid expressing $VPD_0$ breakpoint at 1.5 kPa than that at 2.0 kPa. The water conservation was not directly proportional to the expression of $VPD_0$. Considering an average 1.8 m deep soil with 0.13 volumetric fraction of available soil water, the average difference in FTSW between the hybrids and the reference hybrid translates into 25 mm ($VPD_0$=1.5 kPa) and 17 mm ($VPD_0$=2.0 kPa) of water at anthesis.

Example 6

Environmental Characterization

Figure 6:
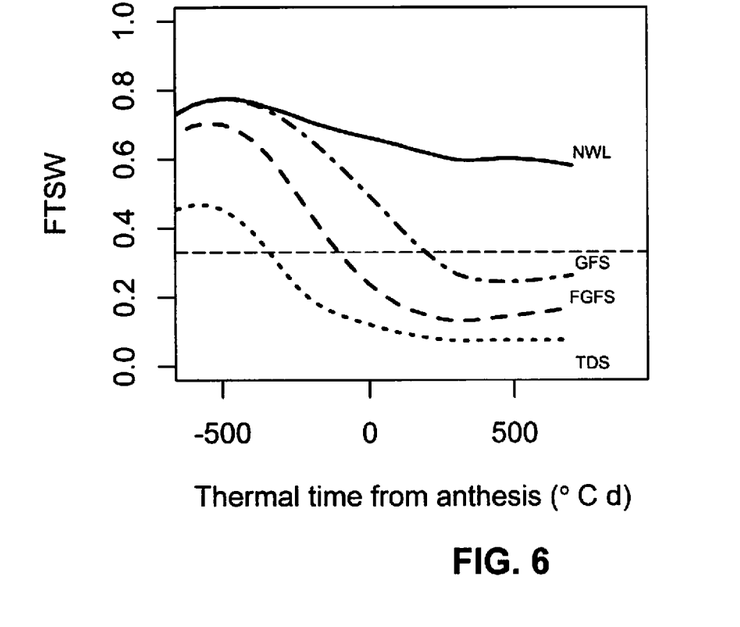
FIG. 6 shows characteristic dynamics of water use estimated from fraction of transpirable soil water (FTSW) for four environment types, no water limitation (NWL), grain fill stress (GFS), flowering and grain fill stress (FGFS), and terminal drought stress (TDS), determined by cluster analyses. The horizontal line indicates the value below which relative transpiration decreases relative to 1. Thermal time (° C.) is calculated as the average between daily maximum and minimum temperature with base temperature for preflowering equal to 8° C. and postflowering equal to 0° C.

An environmental characterization was conducted based on temporal dynamics of FTSW centered on anthesis. The complete set of 163,989 environments that result from the combination of year and location (grid) was analyzed using clustering and 163,161 environments were summarized by grouping the individual environments in groups of "Environment-types" characterized by the average stress pattern: no water limitation (NWL), grain fill stress (GFS), flowering and grain fill stress (FGFS), and terminal drought stress (TDS) (FIG. 6). A small fraction of the simulations, 0.5 percent, terminated during the vegetative phase of crop development and these simulations were excluded from genotype-by-environment-by-management interaction analysis.

Example 7

Value of the Limited-Transpiration Trait Depends on Environment and Management

Analyses of variance of the simulated yields indicated that hybrid, environment, management and their interactions significantly affected yields and the value of the limited-transpiration trait (P<0.001). Simulated yields for both hybrids expressing a breakpoint $VPD_0$ of 2 kPa and the non-limited reference hybrid were largest for environment-type NWL and lowest for environment-type TDS, which on average across all management and genotype combinations were 1487 g m$^{-2}$ and 624 g m$^{-2}$, respectively. Across genotype and environment-type class effects of changes in plant population relative to the normal planting density for the geographical region were significant yet small relative to the effects of environment-type class. Mean simulated yields for Low, Normal and High planting densities were 1078, 1166 and 1217 g m$^{-2}$, respectively. There was a positive difference of 39 g m$^{-2}$ between the hybrid expressing a transpiration limitation ($VPD_0$=2 kPa) and the non-limited reference hybrid across environment-type class and management regimes.

Effects of increasing plant population on simulated yields were positive within environment-type classes NWL, GFS, and FGFS (Table 1). Although the greatest effect of increasing plant population relative to normal density was simulated for a hybrid expressing the breakpoint in environment type class NWL (122 vs. 117 g m$^{-2}$), the highest mean yield was simulated for the reference hybrid (1642 vs. 1572 g m$^{-2}$). In contrast, under severe water limitation a genotype by management interaction was evident. Within environment-type class TDS mean simulated yields decreased from 569 g m$^{-2}$ to 549 g m$^{-2}$ when plant population increased from Low to High for the non-limited reference hybrid, while mean simulated yield increased from 684 m$^{-2}$ to 692 g m$^{-2}$ for the hybrid expressing the trait (Table 1).

The value of the limited-transpiration trait increased with increasing level of water-deficit stress and plant density (Table 1). The largest difference between the hybrid expressing transpiration limitation ($VPD_0$=2.0 kPa) and the non-limited reference hybrid was observed under high plant density within environment-type class TDS (143 g m$^{-2}$), while the largest yield penalty was observed under low plant population within environment-type class NWL (−34 g m$^{-2}$). In GFS environments the trait had negative (positive) impact on yield under low (high) plant population. This significant hybrid by environment by management interaction was consistent with the negative slopes calculated when regressing yield differences on yield for the reference hybrid not expressing the trait (FIG. 3).

TABLE 1

Predicted mean yields (g m$^{-2}$) and yield difference (d) between a hybrid expressing the limited-transpiration trait (LT) and a reference hybrid not expressing any limitation (NLT), by plant population density and environment: no water limitation (NWL), grain fill stress (GFS), flowering and grain fill stress (FGFS), and terminal drought stress (TDS). FIGURE.

| Genotype | Environment type class | | | |
| --- | --- | --- | --- | --- |
| | NWL | GFS | FGFS | TDS |
| | | g m$^{-2}$ | | |
| High density (about 40k-60k/acre) | | | | |
| LT | 1613 | 1480 | 1188 | 692 |
| NLT | 1642 | 1471 | 1107 | 549 |
| d | −29† | 9† | 80† | 143† |
| Normal density | | | | |
| LT | 1492 | 1408 | 1155 | 693 |
| NLT | 1525 | 1408 | 1094 | 558 |
| d | −33† | −0‡ | 60† | 135† |

TABLE 1-continued

Predicted mean yields (g m$^{-2}$) and yield difference (d) between a hybrid expressing the limited-transpiration trait (LT) and a reference hybrid not expressing any limitation (NLT), by plant population density and environment: no water limitation (NWL), grain fill stress (GFS), flowering and grain fill stress (FGFS), and terminal drought stress (TDS). FIGURE.

| Genotype | Environment type class | | | |
|---|---|---|---|---|
| | NWL | GFS | FGFS | TDS |
| | g m$^{-2}$ | | | |
| Low density | | | | |
| LT | 1310 | 1281 | 1090 | 684 |
| NLT | 1344 | 1296 | 1055 | 569 |
| d | −34† | −15† | 35† | 115† |

†P-value < 0.005
‡NS

Example 8

Limiting Transpiration Improves Maize Adaptation to Drought Prone Environments Associated with Shifts in Patterns of Water Use The limited-transpiration trait has consistent value in the Western Corn Belt and parts of the Central-Eastern Corn Belt. Simulated changes in the soil water balance due to the limited-transpiration trait can explain the simulated yield gains and compare well with simulation studies previously conducted for sorghum. The calculated average values between 17 and 25 mm conservation of soil moisture as a result of the trait compares well with soil water measurement differences between a drought tolerant hybrid and a drought susceptible hybrid. Improved drought tolerance underpinned by increased stomata sensitivity to VPD and water conservation was also demonstrated in pearl millet and chickpea. Due to the susceptibility of silk elongation and emergence to water deficit in maize, it is expected that improvements in soil moisture content at anthesis could be conducive to improved kernel set and harvest yield maintenance under severe drought stress. Both of the effects of the trait, shift of water use from vegetative to the reproductive period, and improved kernel set can contribute to the yield improvement.

Example 9

Trait by Management by Environment Interactions and Intensification of Cropping Systems Simulated yield increased with increasing plant density in severe drought stress (environment-type TDS), except for the case of the reference hybrid not expressing the limited-transpiration trait. The increase in simulated yield across environment classes that include drought-prone environments for hybrids expressing the limited-transpiration trait in response to increased plant density can provide a plausible explanation for the widespread trends towards increasing cropping systems intensification across the U.S. maize production regions. In addition, results from the simulation conform well to the observed yield response to plant-density field studies conducted for drought-tolerant and susceptible hybrids. Empirical evidence for increased performance under drought stress and higher than normal plant density was presented for drought tolerant hybrids relative to control hybrids. Yield difference between these two groups of hybrids evaluated in severe-stress environments (26 year-location combinations) increased from 0 g m$^{-2}$ at 2 pl m$^{-2}$ to 50 g m$^{-2}$ at 7 pl m$^{-2}$. The results presented in this study indicate the feasibility for further intensification of maize cropping systems operating in drought-prone regions or under high VPD environments by means of selection for the limited-transpiration trait in maize breeding programs.

Example 10

Benefits of the Limited-Transpiration Trait within Breeding Programs

In well-watered environments (environment-type class 2) and production systems producing yields greater than 1300 g m$^{-2}$ detrimental effects of the limited-transpiration trait were evident and consistent. This prediction conforms well to 1) theory, 2) postulates about the reduction in stomata conductance sensitivity to VPD in response to selection for high productivity in wheat and beans, and 3) the existence of maize hybrids with a linear response of transpiration to VPD. However, contrary to the expectation set on the premise that maize selection in high-yielding environments of the Central-Corn Belt would have decreased stomata sensitivity to VPD, significant genotypic variation in transpiration response to VPD was recently documented for maize elite germplasm.

Results documenting spatial variation (FIG. 3) and genotype by environment by management interactions (Table 1) help reconcile the notion of selection under high productivity environments and the ubiquitous nature of genetic variation for the limited-transpiration trait in maize germplasm, and provides evidence for a functional contribution to the observed long-term trend gain for yield of maize under drought conditions that has been associated with selection for yield in the US Corn Belt environments.

Figure 7:
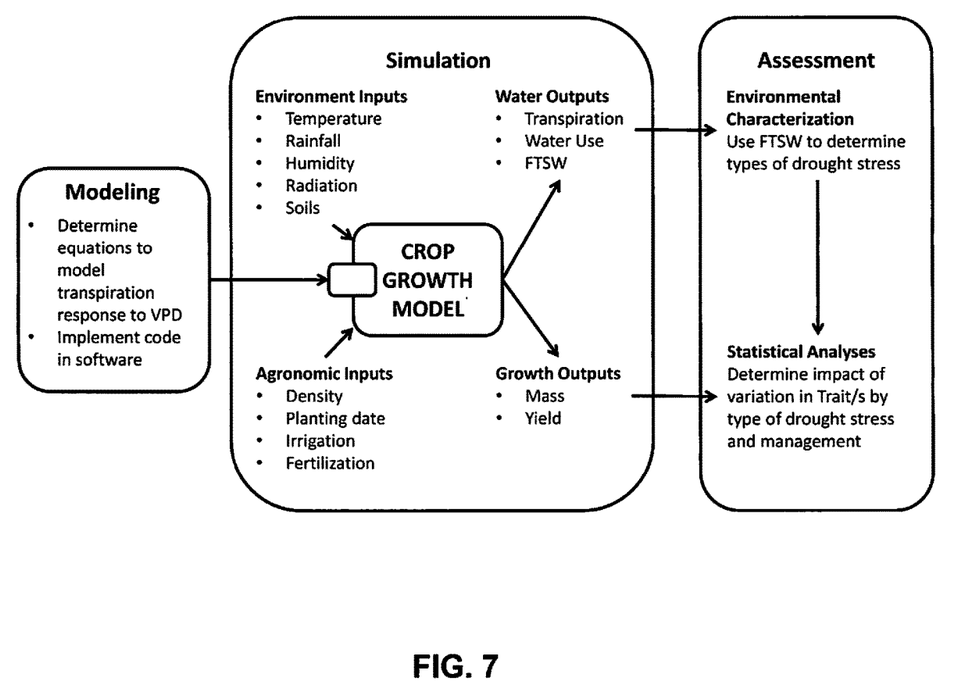
FIG. 7 shows the limited transpiration trait model and the associated simulation parameter.

Limited-transpiration trait is helpful to improve genetic gain achieved in breeding programs—it is expected that the combination of genotype by environment by management interactions and environmental heterogeneity have resulted in positive selection for the limited-transpiration trait in some years and negative selection against the trait in other years. The slight advantage on average and the presence of genotype by environment by management interaction may have contributed to the maintenance of significant genetic variation for the trait in the elite germplasm of the breeding programs. A limited transpiration trait model is shown in FIG. 7, that accounts for several inputs such as environment and other agronomic parameters, can be instrumental to inform selection of plants with desired levels of limited-transpiration trait for target regions.

Mapping the genetic architecture and haplotype diversity of the limited-transpiration trait in the elite germplasm of breeding programs enables further testing of this hypothesis. Results from the studies enable the design and implementation of selection strategies for dealing positively with characterized genotype by environment by management interactions and further leveraging the trait in breeding maize for long-term improved drought tolerance.

Example 11

Limited-Transpiration Trait Expression at Different Temperatures for Maize Hybrids.

Increasing temperature impacts protein activities and membrane permeability and composition. The expression of the limited-transpiration trait may vary among hybrids at high temperatures. Experiments conducted in controlled environments on hybrids known to express the limited-transpiration trait at 32° C. (Table 2) demonstrated that 5 out of 12 of these hybrids lose the capacity to express the limited-transpiration trait at 38° C. (Table 3).

TABLE 2

Summary of experiments: hybrids, day/night growth temperatures, dates of VPD tests, number of replicates in VPD test.

| Hybrids | Day/night growth temperature (° C.) | Date Transpiration vs. VPD test | Replicates per hybrid |
|---|---|---|---|
| Experiment 1 at 38° C. | | | |
| S013 | 31/26 | 11&12 March | 4 |
| S007 | 31/26 | 11&12 March | 4 |
| S010 | 31/26 | 11&12 March | 4 |
| S017 | 31/26 | 8&9 April | 4 |
| S030 | 31/26 | 8&9 April | 4 |
| S004 | 31/26 | 8&9 April | 4 |
| S027 | 31/26 | 22&23 April | 4 |
| S031 | 31/26 | 22&23 April | 4 |
| S024 | 31/26 | 22&23 April | 4 |
| S021 | 31/26 | 29&30 May | 4 |
| S029 | 31/26 | 29&30 May | 4 |
| S019 | 31/26 | 29&30 May | 4 |
| Experiment 2 at 36° C. | | | |
| S013 | 32/26 | 30&31 July | 4 |
| S007 | 32/26 | 13&14 October | 5 |
| S010 | 32/26 | 28&29 July | 4 |
| S017 | 32/26 | 30&31 July | 4 |
| S004 | 32/26 | 28&29 July | 4 |
| S031 | 32/26 | 13&14 October | 5 |
| S024 | 32/26 | 30&31 July | 4 |
| S021 | 32/26 | 28&29 July | 4 |
| Experiment 3 at 34° C. | | | |
| S013 | 32/26 | 15&16 July | 4 |
| S007 | 32/26 | 20&21 October | 5 |
| S010 | 32/26 | 17&18 July | 4 |
| S017 | 32/26 | 17&18 July | 4 |
| S004 | 32/26 | 17&18 July | 4 |
| S031 | 32/26 | 20&21 October | 5 |
| S024 | 32/26 | 15&16 July | 4 |
| S021 | 32/26 | 15&16 July | 4 |
| Experiment 4 at 27.5° C. | | | |
| S013 | 32/26 | 23&24 July | 4 |
| S010 | 32/26 | 21&22 July | 4 |
| S017 | 32/26 | 21&22 July | 4 |
| S004 | 32/26 | 21&22 July | 4 |
| S024 | 32/26 | 23&24 July | 4 |
| S021 | 32/26 | 23&24 July | 4 |

TABLE 3

Genotypic variation in the breakpoint of the transpiration response to vapor pressure deficit (VPD) to changes in temperature (° C.).

| Hybrids | Temperature | | | | | | |
|---|---|---|---|---|---|---|---|
| | 25 | 27.5 | 30 | 32 | 34 | 36 | 38 |
| | | | | | kPa | | |
| S013 | 1.81 | 2.04 ± 0.36 | 2.13 | 1.74 | 2.26 ± 0.20 | 2.01 ± 0.42 | linear |
| S007 | — | — | — | 1.86 | 2.45 ± 0.40 | 2.15 ± 0.40 | linear |
| S010 | 1.75 | 1.62 ± 0.67 | 2.08 | 1.91 | 1.90 ± 0.50 | 1.18 ± 0.34 | linear |
| S017 | 1.86 | 1.80 ± 0.44 | 2.19 | 2.01 | 1.95 ± 0.28 | 2.14 ± 0.47 | 2.60 ± 0.84 |
| S030 | — | — | — | 2.01 | — | — | 3.20 ± 0.24 |
| S004 | — | 2.29 ± 0.15 | — | 2.06 | 2.42 ± 0.10 | 1.62 ± 0.71 | 3.70 ± 0.53 |
| S027 | — | — | — | 2.11 | — | — | 2.26 ± 0.44 |
| S031 | — | — | — | 2.23 | 2.57 ± 0.25 | 2.62 ± 1.13 | linear |
| S024 | — | 1.82 ± 1.00 | — | 2.40 | 2.40 ± 0.24 | 2.16 ± 0.30 | linear |
| S021 | 1.72 | 1.87 ± 0.63 | 2.04 | 2.50 | 2.10 ± 0.26 | 1.23 ± 0.31 | 2.04 ± 1.31 |
| S029 | — | — | — | 2.50 | — | — | 2.05 ± 0.54 |
| S019 | — | — | — | 2.52 | — | — | 1.98 ± 0.28 |

Genotypic variation in the expression of the limited-transpiration trait in maize was observed at different temperatures. Methods to develop and select inbreds and hybrids based on the expression of the limited transpiration trait and depending on the environment in which the maize is to be grown, are disclosed. Hybrids with varying levels of water conservation and heat tolerance via canopy cooling through transpiration are developed. For example, maize hybrids S021 and S027 consistently had low values for the VPD breakpoint in Experiment 1 at 38° C. allowing full expression of the limited-transpiration trait under a range of temperatures, and maximum water conservation, regardless of the temperature regime. In an another instance, if very high temperature is frequent in the target environment, e.g., sufficiently high to threaten plants with heat stress, it may be advantageous to select hybrids that limit the expression of the trait at 38° C. as compared to 32° C. or other temperatures below 38° C. (Table 3). Water conservation under the cooler temperatures, but efficient transpiration (e.g., high rates) when heat may need to be dissipated by transpiration to avoid over-heating of leaves is a suitable trait combination to manage drought stress and heat stress at varying environmental conditions.

What is claimed is:

1. A method to increase maize grain yield in a genetically modified hybrid corn plant grown under drought stress during a reproductive phase period, the method comprises:
   (i) selecting a genetically modified hybrid maize plant from a population of maize germplasm in a maize breeding program using artificial processes in said maize breeding program that expresses a limited transpiration trait based on genotypic determination under increasing vapor pressure deficit and high planting density, wherein said genetically modified hybrid maize plant is obtained by crossing two inbred maize parents in said maize breeding program, wherein the expression of said limited transpiration trait is obtained in said genetically modified hybrid maize plant by one or more genotypic variations introduced during said maize breeding program, wherein said vapor pressure deficit is about 2.0 kPa to about 6.0 kPa, and wherein said introduced one or more genotypic variations are non-transgenic;
   (ii) growing the selected genetically modified hybrid maize plant from step (i) under said drought stress during said reproductive phase period; and (iii) performing genotypic analysis of said selected genetically modified hybrid corn plant from step (ii) to identify that said one or more introduced genotypic variations are inherited, and wherein the expression of the limited transpiration trait shifts water use from a vegetative phase period to the reproductive phase period resulting in improved kernel set, thereby increasing the maize grain yield as compared to a control hybrid maize plant lacking said one or more genotypic variations and grown under similar growth conditions.

2. The method of claim 1, wherein the maize grain yield is about 1300 g/m$^2$ to about 1500 g/m$^2$.

3. The method of claim 1, wherein the limited transpiration trait is expressed at a temperature of about 38° C.

4. The method of claim 1, wherein the limited transpiration trait response to vapor pressure deficit is lost at about 45° C.

5. The method of claim 1, wherein the drought stress is during flowering or grain filling of said reproductive phase period.

6. The method of claim 1, wherein the selected and genetically modified hybrid maize plant exhibits a VPD breakpoint at about 38° C. in a crop growing environment wherein daytime growth temperature ranges from about 35° C. to 40° C.

* * * * *